(12) United States Patent
Vahala

(10) Patent No.: US 10,272,270 B2
(45) Date of Patent: Apr. 30, 2019

(54) COORDINATE TRANSFORMATION OF GRAPHICAL OBJECTS REGISTERED TO A MAGNETIC RESONANCE IMAGE

(71) Applicant: KONINKLIJKE PHILIPS N.V., Eindhoven (NL)

(72) Inventor: Erkki Tapani Vahala, Vantaa (FI)

(73) Assignee: KONINKLIJKE PHILIPS N.V., Eindhoven (NL)

(*) Notice: Subject to any disclaimer, the term of this patent is extended or adjusted under 35 U.S.C. 154(b) by 721 days.

(21) Appl. No.: 14/391,183

(22) PCT Filed: Mar. 28, 2013

(86) PCT No.: PCT/IB2013/052485
§ 371 (c)(1),
(2) Date: Oct. 8, 2014

(87) PCT Pub. No.: WO2013/153477
PCT Pub. Date: Oct. 17, 2013

(65) Prior Publication Data
US 2015/0051517 A1   Feb. 19, 2015

Related U.S. Application Data

(60) Provisional application No. 61/623,097, filed on Apr. 12, 2012.

(30) Foreign Application Priority Data

Apr. 12, 2012   (EP) .................................... 12163926

(51) Int. Cl.
*A61B 5/00*   (2006.01)
*A61N 5/10*   (2006.01)
(Continued)

(52) U.S. Cl.
CPC ................ *A61N 7/00* (2013.01); *A61B 5/055* (2013.01); *A61B 5/742* (2013.01); *A61B 5/7475* (2013.01);
(Continued)

(58) Field of Classification Search
CPC .................................... A61N 7/02; A61N 7/00
See application file for complete search history.

(56) References Cited

U.S. PATENT DOCUMENTS

| | | | | |
|---|---|---|---|---|
| 6,019,725 A | * | 2/2000 | Vesely et al. | 600/447 |
| 2002/0131643 A1 | * | 9/2002 | Fels | G06K 9/00 382/224 |

(Continued)

FOREIGN PATENT DOCUMENTS

| | | |
|---|---|---|
| JP | 2004358264 A | 12/2004 |
| WO | 2010050893 A1 | 5/2010 |
| WO | 2010113050 A1 | 10/2010 |

OTHER PUBLICATIONS

Ries, M. et al "Three Dimensional Motion Compensation for Real-Time MRI Guided Focused Ultrasound Treatment of Abdominal Organs", Proceedings of the International Society for Magnetic Resonance in Medicine, 2009, pp. 443.

(Continued)

*Primary Examiner* — Hien N Nguyen

(57) ABSTRACT

A method of using a medical instrument (300, 400) comprising a magnetic resonance imaging (MRI) system (302). The MRI system acquires (100, 202) first magnetic resonance data (342) and reconstructs (102, 204) a first magnetic resonance image (344, 502). A registration (352) of multiple graphical objects (346, 510, 512) to the first magnetic resonance image is received which defines spatial positions of the multiple graphical objects in the first magnetic resonance image. The method further comprises repeatedly: acquiring (106, 210) second magnetic resonance data (354);

(Continued)

reconstructing (108, 212) a second magnetic resonance image (356, 502'); receiving (110, 214) repositioning coordinates (358, 700) in the second magnetic resonance image for a first group (348, 510) selected from the multiple graphical objects; and determining (112, 216) a coordinate transformation (359, 702) of a second group (350, 512) selected from the multiple graphical objects by applying a coordinate transformation model (364) to the repositioning coordinates.

15 Claims, 9 Drawing Sheets

(51) Int. Cl.
| | |
|---|---|
| A61N 7/00 | (2006.01) |
| A61N 7/02 | (2006.01) |
| A61B 5/055 | (2006.01) |
| A61B 90/00 | (2016.01) |
| G01R 33/48 | (2006.01) |
| G06T 11/00 | (2006.01) |

(52) U.S. Cl.
CPC .............. *A61N 5/1039* (2013.01); *A61N 7/02* (2013.01); *G01R 33/4814* (2013.01); *G06T 11/003* (2013.01); *A61B 2090/364* (2016.02); *A61B 2090/374* (2016.02); *A61N 2007/0052* (2013.01)

(56) References Cited

U.S. PATENT DOCUMENTS

| | | | |
|---|---|---|---|
| 2005/0190955 A1* | 9/2005 | Brown | 382/128 |
| 2008/0033240 A1 | 2/2008 | Hoffman et al. | |
| 2010/0324420 A1 | 12/2010 | Snook et al. | |
| 2011/0152666 A1* | 6/2011 | Shanbhag et al. | 600/411 |
| 2011/0172517 A1 | 7/2011 | Schmidt | |
| 2011/0211718 A1 | 9/2011 | Chua | |
| 2013/0131495 A1 | 5/2013 | Konofagou et al. | |

OTHER PUBLICATIONS

Roujol, Sebastien et al "Automatic Nonrigid Calibration of Image Registration for Real Time MR-Guided HIFU Ablations of Mobile Organs", IEEE Transactions on Medical Imaging, Oct. 2011, vol. 30, No. 10, pp. 1737-1745.

Wolthaus, J.W.H. et al "Treatment plan Evaluation—Comparison of Different Strategies to use 4D CT in Treatment-Planning for lung Cancer Patients", International Journal of Radiation Oncology, Biology and Physics, vol. 70, 2008.

Oguro, Sota et al "Image Registration of Pre-Procedural MRI and Intra-Procedural CT Images to Aid CT-Guided Percutaneous Cryoablation of Renal Tumors" Int. Journal Comput Assist Radiol Surg. Jan. 2011, vol. 6, No. 1, pp. 111-117.

* cited by examiner

COORDINATE TRANSFORMATION OF GRAPHICAL OBJECTS REGISTERED TO A MAGNETIC RESONANCE IMAGE

CROSS-REFERENCE TO PRIOR APPLICATIONS

This application is the U.S. National Phase application under 35 U.S.C. § 371 of International Application No. PCT/IB2013/052485, filed on Mar. 28, 2013, which claims the benefit of U.S. Provisional Patent Application No. 61/623,097, filed on Apr. 12, 2012 and European Patent Application No. 12163926.4, filed on Apr. 12, 2012. These applications are hereby incorporated by reference herein.

TECHNICAL FIELD

The invention relates to magnetic resonance imaging, in particular to the registration of graphical objects to the magnetic resonance image.

BACKGROUND OF THE INVENTION

In High Intensity Focused Ultrasound (HIFU), a volume of interest is detected during the planning stages and may be marked on medical images, such as magnetic resonance images. For example, an ellipsoid can be quickly drawn over a uterine fibroid. Volumes to be destroyed, so called treatment cells, can be planned in advance and may landmark vessels or other structures to be destroyed. Regions of interest can be drawn to highlight organs at risk and safety margins to organ structures. Once sonications have been carried out, the produced temperature map overlays and thermal doses correspond to signal changes in images where the tissue has been altered with thermal energy. These form the basic HIFU graphical objects. The international application WO2010/113050 discloses delineating anatomical features in images used for image-guided therapy planning. This known delineation makes use of a comparison of the position of anatomical landmarks in the image to reference landmarks.

However, subjects may have external and/or internal motion during a course of sonication. Automatic re-registration algorithms are susceptible to errors when the input image data does not provide sufficient/correct contrast or signal to noise ratio. Landmark-based manual methods need extensive user interaction to define suitable anatomical landmarks and slow down the therapy session. The ISMRM abstract in Proc. ISMRM(2009)443 mentions that a 2D selective navigator is employed to compensate out-of-plane motion.

SUMMARY OF THE INVENTION

The invention provides for a medical instrument, a computer program product, and a method of controlling the medical instrument in the independent claims. Embodiments are given in the dependent claims.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCPIP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprising a magnetic resonance imaging system for acquiring magnetic resonance data from an imaging zone. The medical instrument further comprises a processor for controlling the medical instrument. The medical instrument further comprises a memory containing machine-readable instructions for execution by the processor. Execution of the instructions causes the processor to acquire first magnetic resonance data with the magnetic resonance imaging system. The first magnetic resonance data is magnetic resonance data. Execution of the instructions further causes the processor to reconstruct a first magnetic resonance image using the first magnetic resonance data. The first magnetic resonance image is a magnetic resonance image.

A magnetic resonance image as used herein encompasses data which may be used to render or display an image on a display. For instance the magnetic resonance image may comprise data which represents a slice, a single voxel, or even a three-dimensional volume. Execution of the instructions further causes the processor to receive a registration of multiple graphical objects to the first magnetic resonance image. The registration defines spatial positions of the multiple graphical objects with respect to the first magnetic resonance image. Execution of the instructions further causes the processor to repeatedly acquire second magnetic resonance data using the magnetic resonance imaging system.

The second magnetic resonance data is magnetic resonance data. Execution of the instructions further causes the processor to repeatedly reconstruct a second magnetic resonance image using the second magnetic resonance data. The second magnetic resonance image is also a magnetic resonance image. Execution of the instructions further cause the processor to receive positioning coordinates in the second magnetic resonance image for a first group selected from the multiple graphical objects. The repositioning coordinates describe a repositioning of the first group in the second magnetic resonance image with respect to the first magnetic resonance image. It is in other words to say that the position of the multiple graphical objects is defined in the first magnetic resonance image.

When the second magnetic resonance image is reconstructed the multiple graphical objects may not be properly registered with the second magnetic resonance image. The repositioning coordinates describe the new position of the first group of multiple graphical objects. The first group may for instance contain one or more of the multiple graphical objects. Execution of the instructions further cause the processor to repeatedly determine a coordinate transformation of a second group selected from the multiple graphical objects by applying a coordinate transformation model to the repositioning coordinates. An insight of the invention is that in the treatment plan formed from the first magnetic resonance image contains suitable graphical objects that can be employed to derive motion. The graphical objects in the treatment plan per se could for example be delineated in the first magnetic resonance image by way of the approach in the international application WO2010/113050. That known approach, however, limits its application to automatic delineation of anatomy in image guided therapy planning. That is, the known approach is applied only in the original generation of the therapy plan. The present invention is based on the insight that the same graphical objects can be employed to detect movement and accordingly correct the treatment plan. By registering the corresponding graphical objects in the first magnetic resonance image to those in the second magnetic resonance image a coordinate transformation is found that represents the motion that occurred between the first magnetic resonance image that forms the basis of the treatment plan and the subsequent second magnetic resonance image. This coordinate transformation is then employed to modify or update the treatment plan to account for the motion that has occurred. The high-instensity focused ultrasound system is continued to be controlled on the basis of the modified treatment plan. For example the adjustable focus is moved so as to account for the motion that has occurred. In this way even if motion occurs, the high-intensity focused ultrasound radiation remains focused into a target zone that is to be treated and deposition of energy surrounding healthy tissue is avoided. Thus, hyperthermia is accurately applied to the tissue in the target region even if motion occurs. Because the graphical objects contained in the treatment plan are used, there is no need to separately select graphical objects. Notably, the graphical objects in the treatment plan represent relevant anatomical structures of which the motion is taken into account in the update of the treatment plan.

This embodiment may be beneficial because it provides for a means of properly positioning the multiple graphical objects on the second magnetic resonance image. One or more of the multiple graphical objects are first repositioned and then a coordinate transformation model is used to reposition one or more of the remaining multiple graphical objects based on the way the first repositioning was performed. This may provide for a means of repositioning the multiple graphical objects in the second magnetic resonance image for instance when a subject moves. For instance, the first and second magnetic resonance data may be acquired from a subject.

In another embodiment execution of the instructions further causes the processor to receive a treatment plan for controlling a high-intensity focused ultrasound system with an adjustable focus. A treatment plan as used herein encompasses a set of instructions or data which may be used for generating a set of instructions for operating the high-intensity focused ultrasound system. In some embodiments the treatment plan may contain anatomical or other data descriptive of the subject.

Execution of the instructions further causes the processor to repeatedly modify the treatment plan using the repositioning coordinates and the coordinate transformation. This embodiment may be beneficial because it provides for a means of correcting the position of the multiple graphical objects which specify a location such as regions to sonicate and/or protect from heating.

In another embodiment the medical instrument further comprises the high-intensity focused ultrasound system. Execution of the instructions further cause the processor to control the high-intensity focused ultrasound system in accordance with the treatment plan. This embodiment may be beneficial because the treatment plan used to control the high-intensity focused ultrasound system is updated using the repositioning coordinates and the coordinate transformation.

In another embodiment execution of the instructions further cause the processor to perform a reduced intensity sonication before acquisition of the first magnetic resonance data. Execution of the instructions causes the processor to check the registration using the first magnetic resonance image. This embodiment may be beneficial because the reduced intensity sonication may be a test shot for determining if the registration between the image and the high-intensity focused ultrasound system is correct or not.

In another embodiment the coordinate transformation model is a deformable shape model. A deformable shape model as used herein encompasses a model descriptive of a subject's internal structure which uses a least energy or other algorithm to fit the model to the actual geometry in a magnetic resonance image.

In another embodiment each of the graphical objects has a tag. The coordinate transformation of the second group is determined at least partially using the tag of each of the second group. For instance the graphical objects may have a type or tag which may be used to identify the type of graphical objects or some of its properties. For instance considering the case of a subject who is breathing within the abdominal cavity the organs may move around considerably during the process of the subject breathing or working. By using a tag the particular graphical object may be classified as to an anatomical region it is nearby and this may aid in choosing a model to predict its motion or for instance points on a subject's skin could be selected and in this case the motion of the tags may be limited.

In another embodiment the graphical objects are any one of the following: treatment cells, regions of interest, measured doses, planned target volumes, and combinations thereof.

In another embodiment the memory further contains an image selection module containing machine-readable instructions for execution by the processor for segmenting the magnetic resonance image to determine the repositioning coordinates. Execution of the instructions further causes the processor to receive the repositioning coordinates from the segmentation module. In this embodiment the position of the first group is determined automatically using the segmentation module. In some embodiments, the segmentation module can be used to identify and/or tag objects. Tagging an object may be equivalent to classifying the objects. The classification may then be used by a particular coordinate transformation model the new coordinates in response to the repositioning coordinates. This may provide for more accurate and timely updating of the treatment plan.

In another embodiment execution of the instructions further causes the processor to repeatedly display the second magnetic resonance image on a display. The repositioning coordinates are received from a user interface in response to displaying the second magnetic resonance data.

In another embodiment execution of the instructions further causes the processor to display the first magnetic resonance image on the display. The registration is received from the user interface and responds to displaying the first magnetic resonance data.

In another aspect the invention provides for a computer program product comprising machine-executable instructions for execution by a processor controlling the medical instrument. The medical instrument comprises a magnetic resonance imaging system for acquiring magnetic resonance data from an imaging zone. Execution of the instructions further causes the processor to acquire first magnetic resonance data with the magnetic resonance imaging system. Execution of the instructions further causes the processor to reconstruct a first magnetic resonance image using the first magnetic resonance data. Execution of the instructions further causes the processor to receive a registration of multiple graphical objects to the first magnetic resonance image. The registration defines spatial positions of the multiple graphical objects with respect to the first magnetic resonance image. Execution of the instructions further causes the processor to repeatedly acquire second magnetic resonance data using the magnetic resonance imaging system.

Execution of the instructions further causes the processor to repeatedly reconstruct a second magnetic resonance image using the second magnetic resonance data. Execution of the instructions further causes the processor to repeatedly receive repositioning coordinates in the second magnetic resonance image for a first group selected from the multiple graphical objects. The repositioning coordinates describe a repositioning of the first group in the second magnetic resonance image with respect to the first magnetic resonance image. Execution of the instructions further cause the processor to repeatedly determine a coordinate transformation of a second group selected from the multiple graphical objects by applying a coordinate transformation model to the repositioning coordinates.

In another embodiment execution of the instructions causes the processor to receive a treatment plan for controlling a high-intensity focused ultrasound system with an adjustable focus. Execution of the instructions further causes the processor to repeatedly modify the treatment plan using the repositioning coordinates and the coordinate transformation.

In another embodiment the medical instrument further comprises the high-intensity focused ultrasound system. Execution of the instructions further causes the processor to control the high-intensity focused ultrasound system in accordance with the treatment plan.

In another aspect the invention provides for a method of controlling the medical instrument. The medical instrument comprises a magnetic resonance imaging system for acquiring magnetic resonance data from and imaging zone. The method comprises the steps of acquiring first magnetic resonance data with the magnetic resonance imaging system. The method further comprises the step of reconstructing a first magnetic resonance image using the first magnetic resonance data. The method further comprises the step of receiving a registration of multiple graphical objects to the first magnetic resonance image. The registration defines spatial positions of the multiple graphical objects with respect to the first magnetic resonance image.

The method further comprises repeatedly performing the step of acquiring second magnetic resonance data using the magnetic resonance imaging system. The method further comprises repeatedly performing the step of reconstructing a second magnetic resonance image using the second magnetic resonance data. The method further comprises the step of repeatedly receiving repositioning coordinates in a second magnetic resonance image for a first group selected from the multiple graphical objects. The repositioning coordinates describe a repositioning of the first group in the second magnetic resonance image with respect to the first magnetic resonance image. The method further comprises the step of repeatedly determining a coordinate transformation of a second group selected from the multiple graphical objects by applying a coordinate transformation model to the repositioning coordinates.

In another embodiment the method further comprises the step of receiving a treatment plan for controlling a high-intensity focused ultrasound system with an adjustable focus. The method further comprises the step of modifying the treatment plan using the repositioning coordinates and the coordinate transformation.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
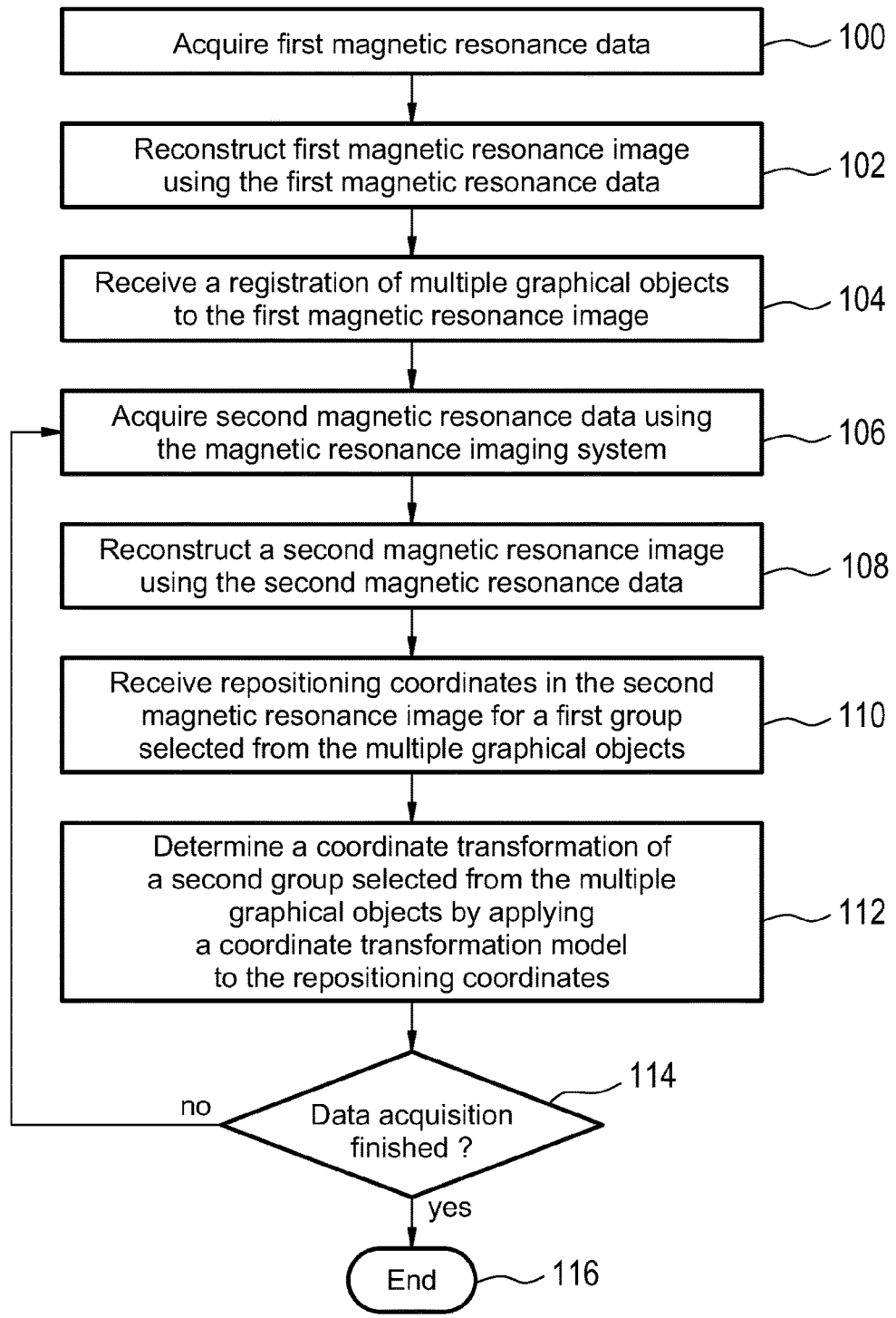
FIG. 1 shows a flow diagram which illustrates an example of a method.

FIG. 1 shows a flow diagram which illustrates an example of a method. First in step 100 first magnetic resonance data is acquired using a magnetic resonance imaging system. Next in step 102 a first magnetic resonance image is reconstructed using the first magnetic resonance data. Next in step 104 a registration of multiple graphical objects is received for the first magnetic resonance image. The registration may for instance come from an automatic segmentation module or it may also be received from a user interface. For instance the first magnetic resonance image may be displayed and a user may manually place the multiple graphical objects on the first magnetic resonance image thereby registering them. Next in step 106 second magnetic resonance data is acquired using the magnetic resonance imaging system. Then in step 108 a second magnetic resonance image is reconstructed using the second magnetic resonance data. Next in step 110 repositioning coordinates are received for a first group of objects selected from the multiple graphical objects. The repositioning coordinates identifies the position of the first group in the second magnetic resonance image. Next in step 112 a coordinate transformation of a second group selected from the multiple graphical objects is determined by applying a coordinate transformation model to the repositioning coordinates. Next box 114 is a decision box, is the data acquisition finished. If the answer is yes then the method ends in step 116. If it is no then the method returns to step 106 where second magnetic resonance data is acquired. The method then proceeds as previously described and repeats until the decision in step 114 is yes.

Figure 2:
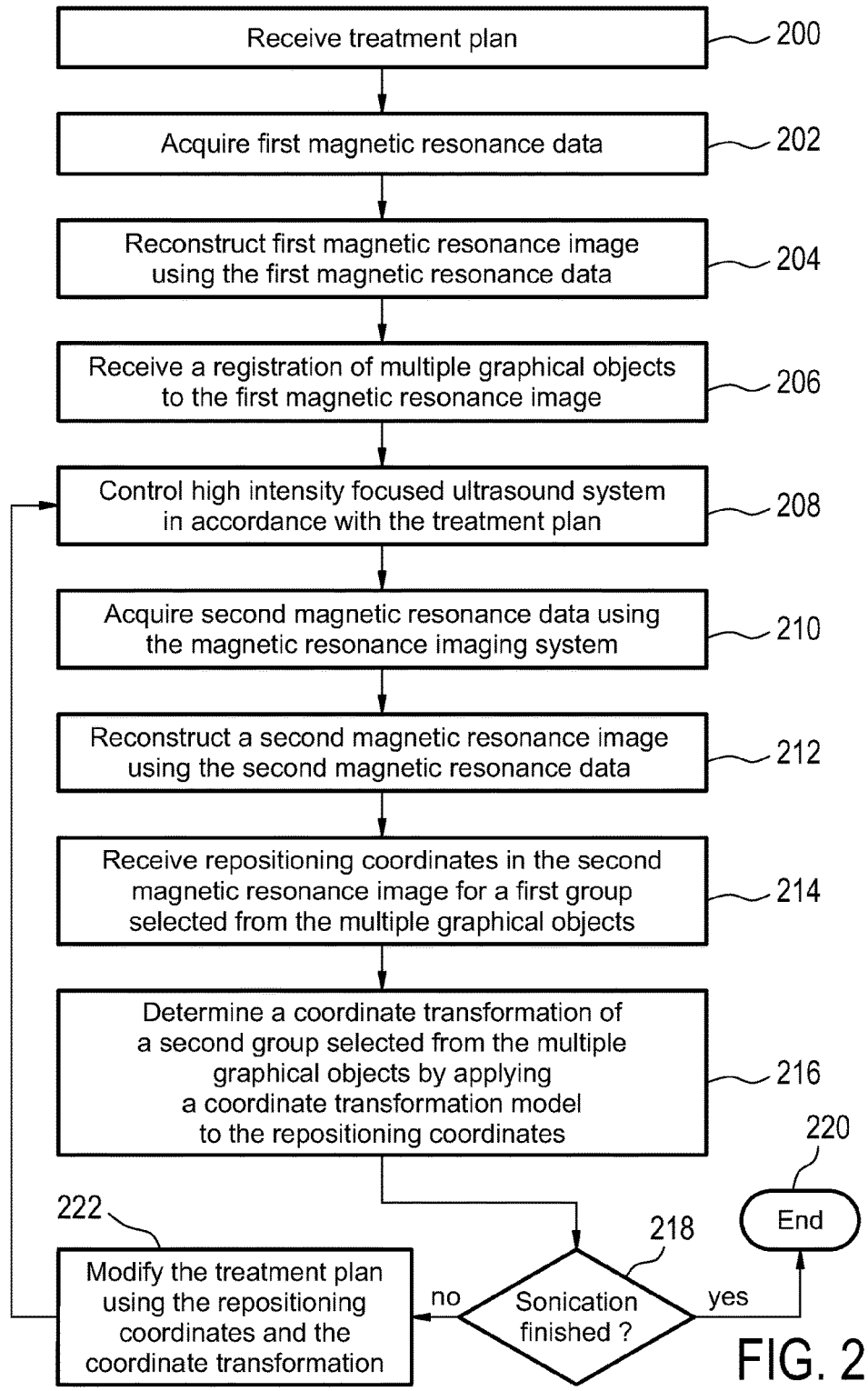
FIG. 2 shows a flow diagram which illustrates a further example of a method.

FIG. 2 shows a flow diagram which illustrates a further example of a method. First in step 200 a treatment plan is received. The treatment plan may contain data useful for constructing control commands for a high-intensity focused ultrasound system or itself may contain commands for controlling a high-intensity focused ultrasound system. Next in step 202 first magnetic resonance data is acquired using a magnetic resonance imaging system. Then in step 204 a first magnetic resonance image is reconstructed using the first magnetic resonance data. Next in step 206 a registration is received of multiple graphical objects in the first magnetic resonance image. Next in step 208 the high-intensity focused ultrasound system is controlled in accordance with the treatment plan. Then in step 210 second magnetic resonance data is acquired using the magnetic resonance imaging system. Next in step 212 a second magnetic resonance image is reconstructed using the second magnetic resonance data. Next in step 214 repositioning coordinates are received in the second magnetic resonance image for a first group selected from the multiple graphical objects.

Next in step 216 a coordinate transformation is determined for a second group selected from the multiple graphical objects by applying a coordinate transformation model to the repositioning coordinates. Next step 218 is a decision box. The question is sonication finished. If the answer is yes then the method ends in step 220. If the answer is no then in step 222 the treatment plan is modified using the repositioning coordinates and the coordinate transformation. The method then proceeds back to step 208 where the high-intensity focused ultrasound system is controlled in accordance with the treatment plan. The method then proceeds as described previously and repeats until in step 218 it is indicated that the sonication is finished and the method ends at step 220. The method described in FIG. 2 forms a closed control loop for control of the high-intensity focused ultrasound system.

Figure 3:
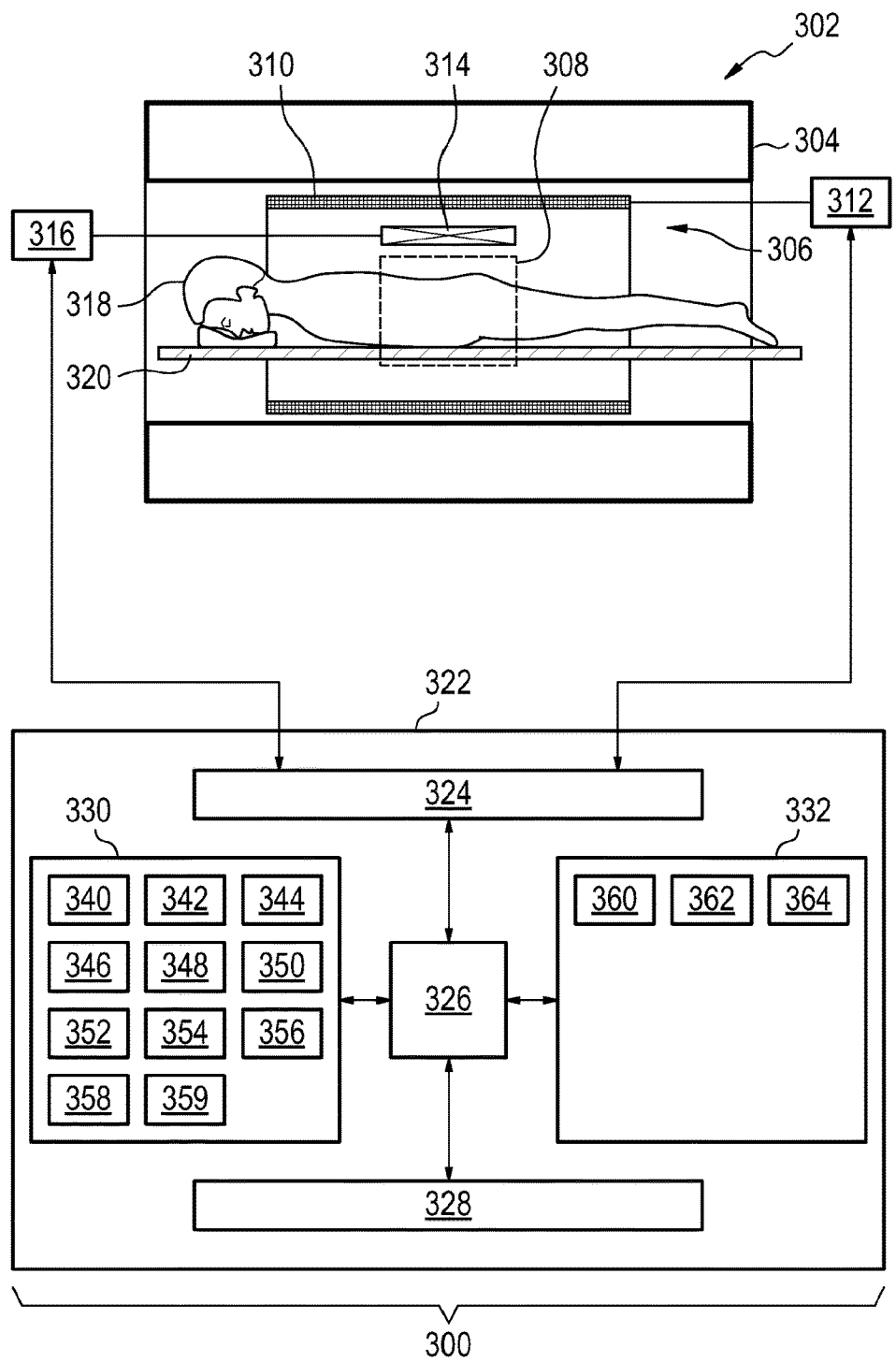
FIG. 3 illustrates an example of a medical apparatus.

FIG. 3 illustrates a medical apparatus 300 according to an embodiment of the invention. The medical apparatus 300 comprises a magnetic resonance imaging system 602. The magnetic resonance imaging system 302 is shown as comprising a magnet 304. The magnet 304 is a cylindrical type superconducting magnet with a bore 306 through the center of it. The magnet 304 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging.

Also within the bore 306 of the magnet is a magnetic field gradient coil 310 which is used for acquisition of magnetic resonance data to spatially encode magnetic spins within an imaging zone of the magnet. The magnetic field gradient coil 310 is connected to a magnetic field gradient coil power supply 312. The magnetic field gradient coil is representative. Typically magnetic field gradient coils contain three separate sets of coils for spatially encoding in three orthogonal spatial directions. A magnetic field gradient power supply 312 supplies current to the magnetic field gradient coils. The current supplied to the magnetic field coils is controlled as a function of time and may be ramped and/or pulsed.

Adjacent the imaging zone 308 is a radio-frequency coil 314. The radio-frequency coil 314 is connected to a radio-frequency transceiver 316. Also within the bore of the magnet 304 is a subject 318 that is reposing on a subject support 320 and is partially within the imaging zone 308.

Adjacent to the imaging zone 308 is a radio-frequency coil 314 for manipulating the orientations of magnetic spins within the imaging zone 308 and for receiving radio transmissions from spins also within the imaging zone 308. The radio-frequency coil 314 may contain multiple coil elements. The radio-frequency coil 314 may also be referred to as a channel or an antenna. The radio-frequency coil is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio-frequency transceiver 316 are representative. The radio-frequency coil 314 is intended to also represent a dedicated transmit antenna and a dedicated receive antenna. Likewise the transceiver 316 may also represent a separate transmitter and a separate receiver.

The magnetic field gradient coil power supply 312 and the radio-frequency transceiver 316 are connected to a hardware interface 324 of a computer system 322. The computer system 322 further comprises a processor 326. The processor 326 is connected to the hardware interface 324. The hardware interface 324 enables the processor 326 to send and receive data and commands to the magnetic resonance imaging system 302. The computer system 322 further comprises a user interface 328, computer storage 330 and computer memory 332.

The computer storage 330 is shown as containing a pulse sequence 340. The pulse sequence 340 contains instructions or data which may be used for generating instructions for controlling the operation and function of the magnetic resonance imaging system 302. The computer storage 330 is shown as further containing first magnetic resonance data that was acquired using the pulse sequence 340. The computer storage 330 is shown as further containing a first magnetic resonance image 344 which was reconstructed from the first magnetic resonance data 342. The computer storage 330 is further shown as containing multiple graphical objects. The computer storage 330 is further shown as containing a first group or an identification of a first group 348 within the multiple graphical objects 346.

The computer storage 330 is further shown as containing a second group 350 or an identification of a second group 350 chosen from the multiple graphical objects 346. The computer storage 330 is shown as further containing an image registration 352 of the multiple graphical objects 346 in the first magnetic resonance image 344. The computer storage 330 is further shown as containing a second magnetic resonance data 354. The computer storage 330 is shown as further containing a second magnetic resonance image 356 reconstructed from the second magnetic resonance data 354. The computer storage 330 is further shown as containing repositioning coordinates 358 which identify the location of the first group 348 within the second magnetic resonance image 356. The computer storage 330 is shown as further containing a coordinate transformation 358 which identifies the location of the second group 350 within the second magnetic resonance image 356.

The computer memory 332 is shown as containing a control module 360. The control module 360 comprises computer-executable code which enables the processor 326 to control the operation and function of the magnetic resonance imaging system 302. For instance it may use the pulse sequence 340 for acquiring the magnetic resonance data 342, 354. The computer memory 332 is further shown as containing an image reconstruction module 362. The image reconstruction module 362 enables the processor to reconstruct the first magnetic resonance image 344 from the first magnetic resonance data 342. The image reconstruction module 362 also enables the reconstruction of the second magnetic resonance image 356 from the second magnetic resonance data 354. The computer memory 332 is further shown as containing a coordinate transformation module 364 which enables the processor 362 to calculate the coordinate transformation 359 using the repositioning coordinates 358.

Figure 4:
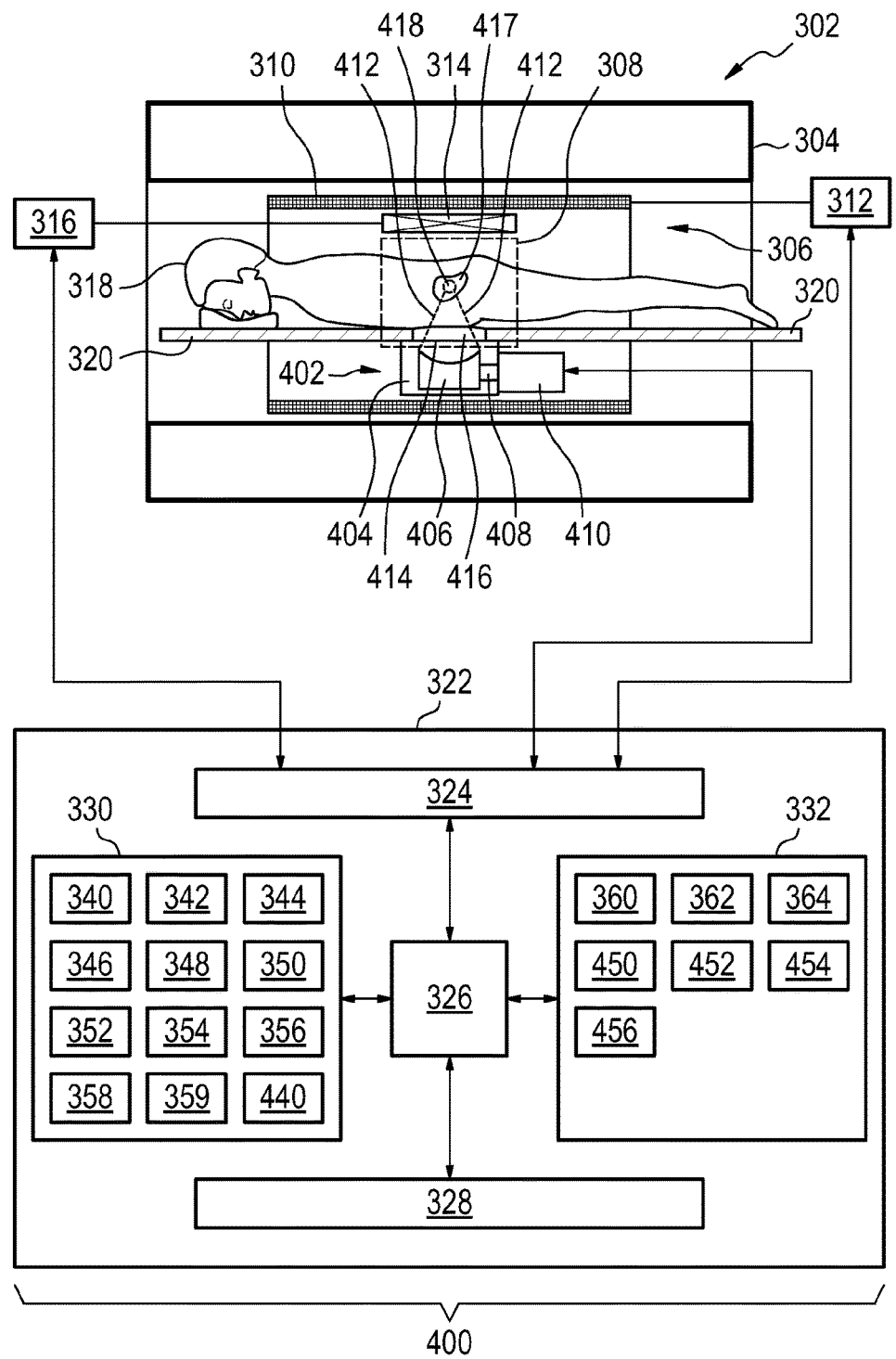
FIG. 4 illustrates a further example of a medical apparatus.

FIG. 4 shows a further embodiment of the medical apparatus 400 according to the invention. In this embodiment the heating system is a high-intensity focused ultrasound system 402. The high-intensity focused ultrasound system comprises a fluid-filled chamber 404. Within the fluid-filled chamber 404 is an ultrasound transducer 406. Although it is not shown in this Fig. the ultrasound transducer 406 may comprise multiple ultrasound transducer elements each capable of generating an individual beam of ultrasound. This may be used to steer the location of a sonication point 418 electronically by controlling the phase and/or amplitude of alternating electrical current supplied to each of the ultrasound transducer elements. The sonication point 418 is operable to be controlled to sonicate the target zone 417.

The ultrasound transducer 406 is connected to a mechanism 408 which allows the ultrasound transducer 406 to be repositioned mechanically. The mechanism 408 is connected to a mechanical actuator 410 which is adapted for actuating the mechanism 408. The mechanical actuator 410 also represents a power supply for supplying electrical power to the ultrasound transducer 406. In some embodiments the power supply may control the phase and/or amplitude of electrical power to individual ultrasound transducer elements. In some embodiments the mechanical actuator/power supply 410 is located outside of the bore 306 of the magnet 304.

The ultrasound transducer 406 generates ultrasound which is shown as following the path 412. The ultrasound 412 goes through the fluid-filled chamber 404 and through an ultrasound window 414. In this embodiment the ultrasound then passes through a gel pad 416. The gel pad is not necessarily present in all embodiments but in this embodiment there is a recess in the subject support 320 for receiving a gel pad 416. The gel pad 416 helps couple ultrasonic power between the transducer 406 and the subject 318. After passing through the gel pad 416 the ultrasound 412 passes through the subject 318 and is focused to a sonication point 418. The sonication point 418 is being focused within a target zone 418. The sonication point 418 may be moved through a combination of mechanically positioning the ultrasonic transducer 406 and electronically steering the position of the sonication point 418 to treat the entire target zone 418.

The high-intensity focused ultrasound system 402 is shown as being also connected to the hardware interference 324 of the computer system 322. The computer system 322 and the contents of its storage 330 and memory 332 are equivalent to that as shown in FIG. 3.

In this example the computer storage 330 is shown as additionally containing a treatment plan 440. The computer memory 332 is shown as additionally containing a high-intensity focused ultrasound system control module 450. The high-intensity focused ultrasound system control module 450 contains computer-executable code which enables the processor 326 to control the high-intensity focused ultrasound system 402 using the treatment plan 440. The computer memory 332 is shown as further containing a treatment plan modification module 452. The treatment plan modification module 452 contains computer-executable code which enables the processor 326 to modify the treatment plan 440 using the repositioning coordinates 358 and the coordinate transformation 359.

The computer memory 332 is shown as further containing an image segmentation module 454. The image segmentation module 454 is not present in all examples and enables the processor 326 to generate the image registration 352 using the first magnetic resonance image 344. The computer memory 332 is further shown as containing a user interface control module 456. The user interface control module 456 may or may not be present in all examples. The user interface control module 456 contains computer executable code which enables the processor 326 to display the second magnetic resonance image 356 on a display and receive repositioning coordinates 358 from a user interface, for example a graphical user interface.

Figure 5:
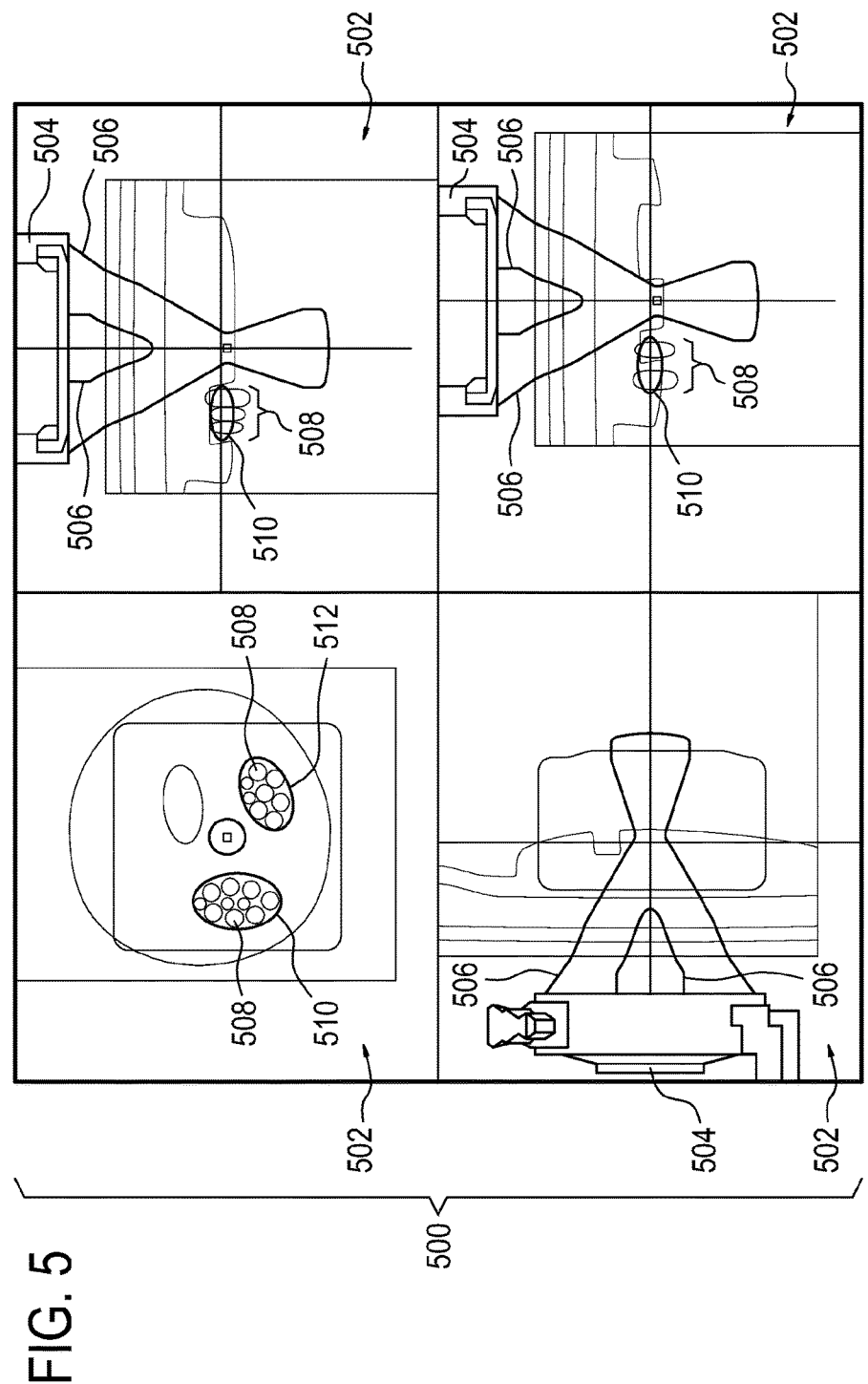
FIG. 5 illustrates an example of a user interface.

FIG. 5 shows a portion of a graphical user interface 500. The graphical user interface 500 displays a number of first magnetic resonance images 502. On some of these images a model of a high-intensity focused ultrasound transducer 504 can be observed. The path of the ultrasound 506 is also indicated on some of these Figs. There are a number of sonication volumes 508 indicated on the various Figs. A first graphical object 510 and a second graphical object 512 are also indicated.

Figure 6:
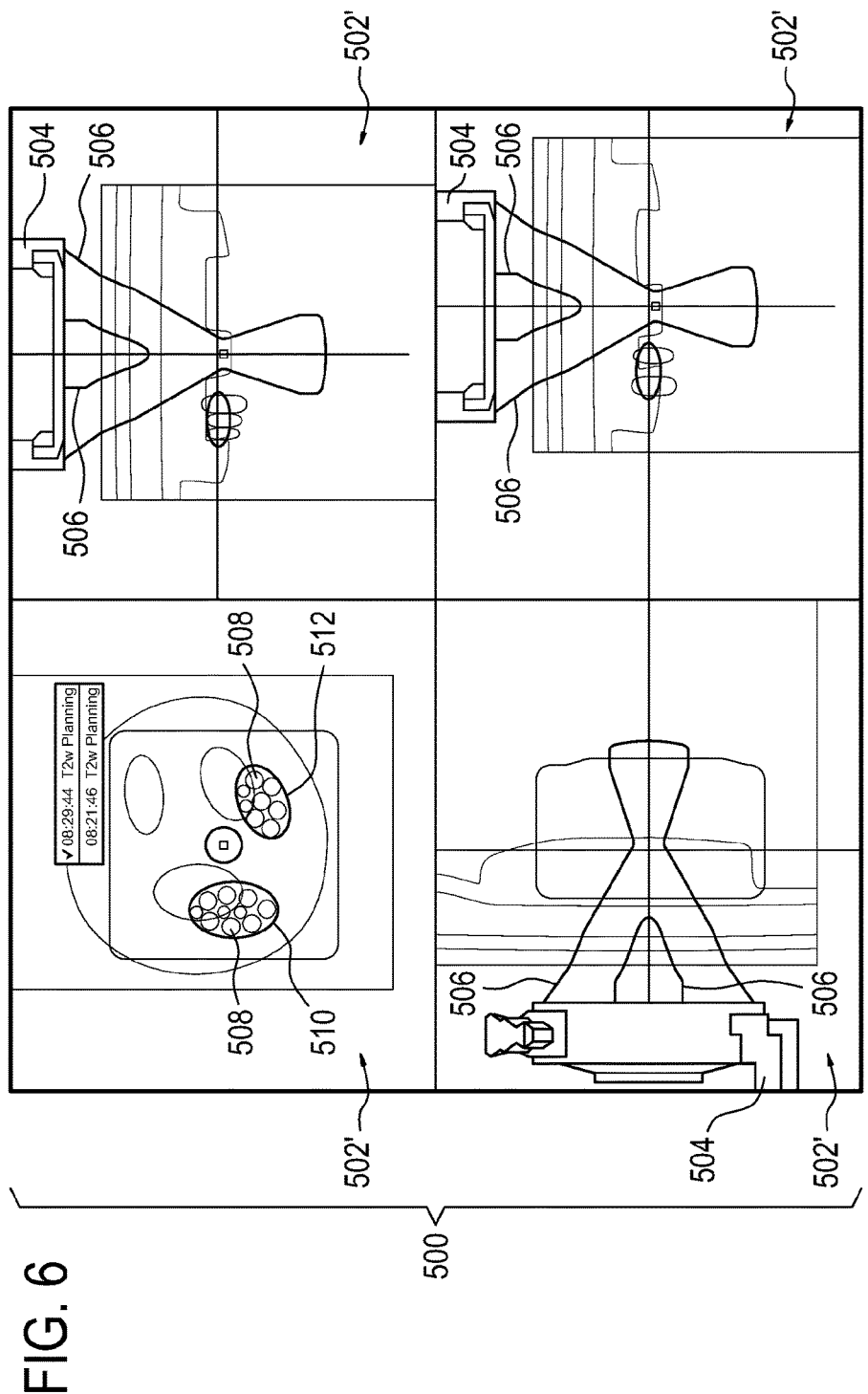
FIG. 6 illustrates a further example of a user interface.

FIG. 6 shows a view of the same graphical interface except a later magnetic resonance image has been acquired. The new magnetic resonance images are second magnetic resonance and are indicated by 502'. It can be seen that the first graphical object 510 and the second graphical object 512 have shifted with respect to the magnetic resonance image 502'. This may be representative of a subject moving during or between sonications. If the sonication volumes 508 are sonicated they will be performed in a location that is different from the original anatomical position shown in FIG. 5.

Figure 7:
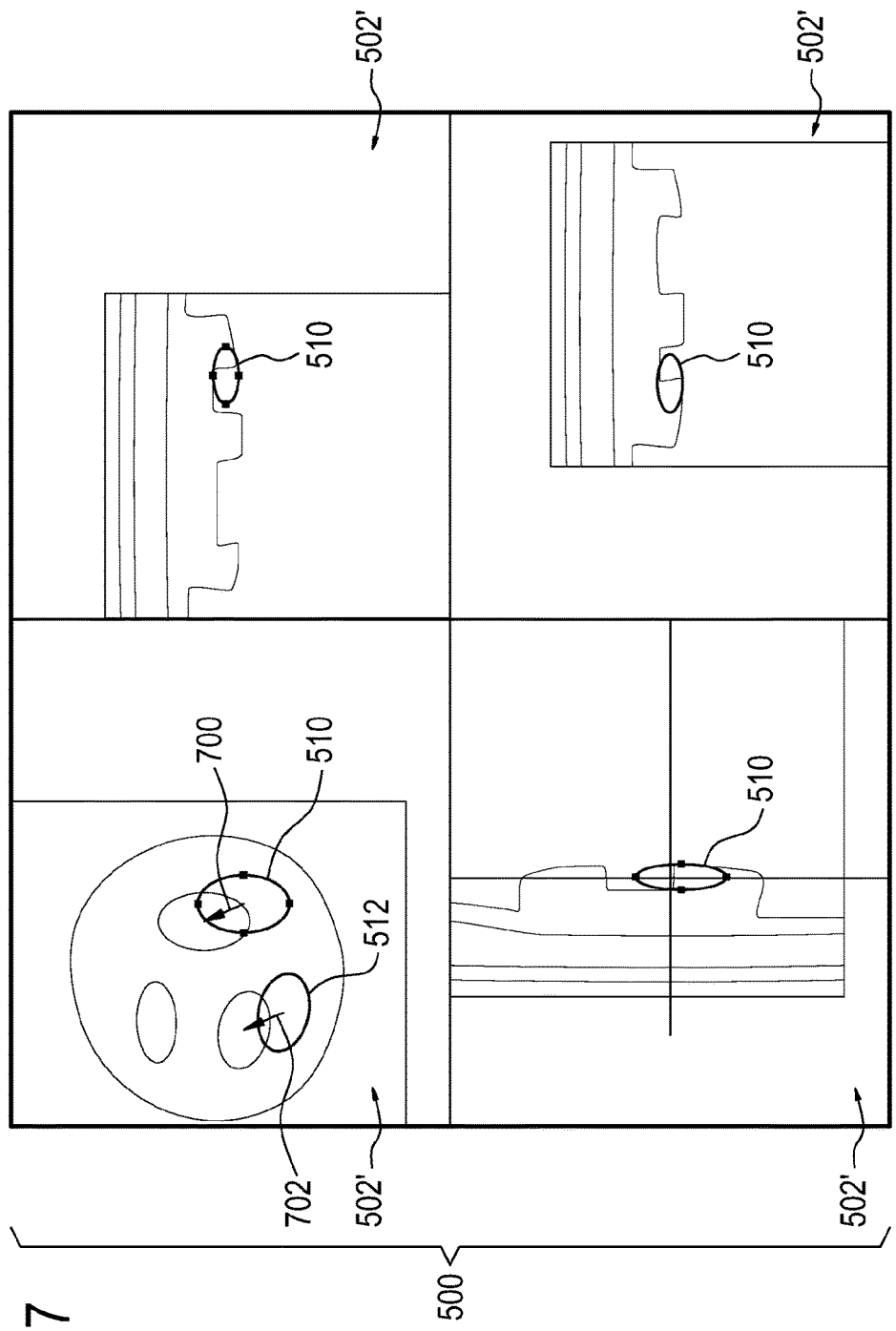
FIG. 7 illustrates a further example of a user interface.

In FIG. 7 the graphical user interface 500 is again displayed. In this example the first graphical object 510 is selected and is repositioned in the magnetic resonance image 502'. The first graphical object 510 is therefore the first group. The second graphical object 512 forms the second group. A transformation 700 correcting the position of the first graphical object 510 is indicated in FIG. 7 and is equivalent to the repositioning coordinates. A transformation 702 correcting the position of the second graphical object 512 is also indicated in FIG. 7 and is equivalent to the coordinate transformation. Some of the images shown in FIG. 7 are shown from a different plane with respect to images in FIGS. 5, 6, 8, and 9 and with different orientations.

Figure 8:
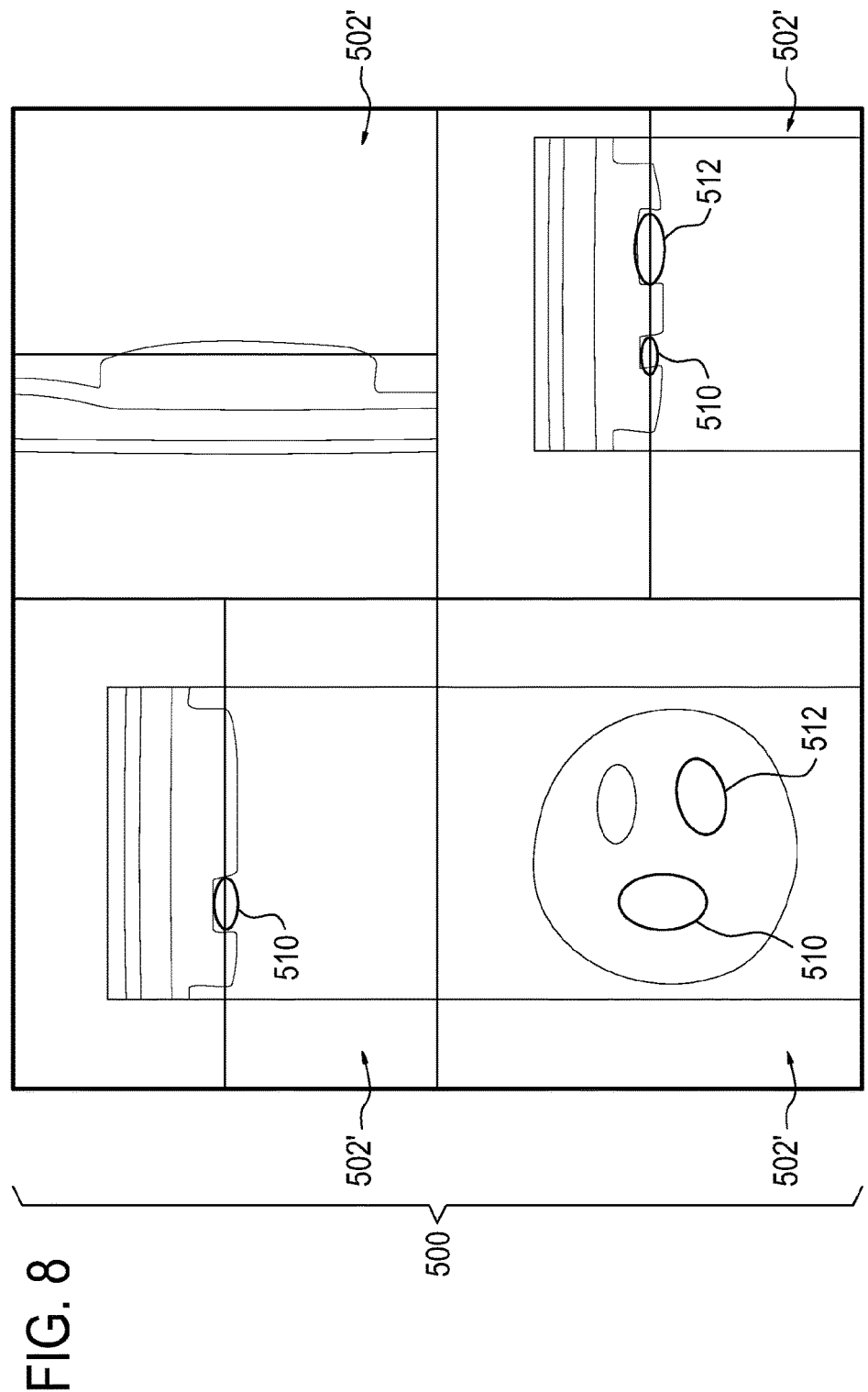
FIG. 8 illustrates a further example of a user interface.

In FIG. 8 the first graphical object 510 has been moved back into its correct position and is properly registered to the magnetic resonance image 502'. The first graphical object 510 is moved to the position set in three different images. The position of the second graphical object 512 has been updated automatically by applying a coordinate transformation model.

Figure 9:
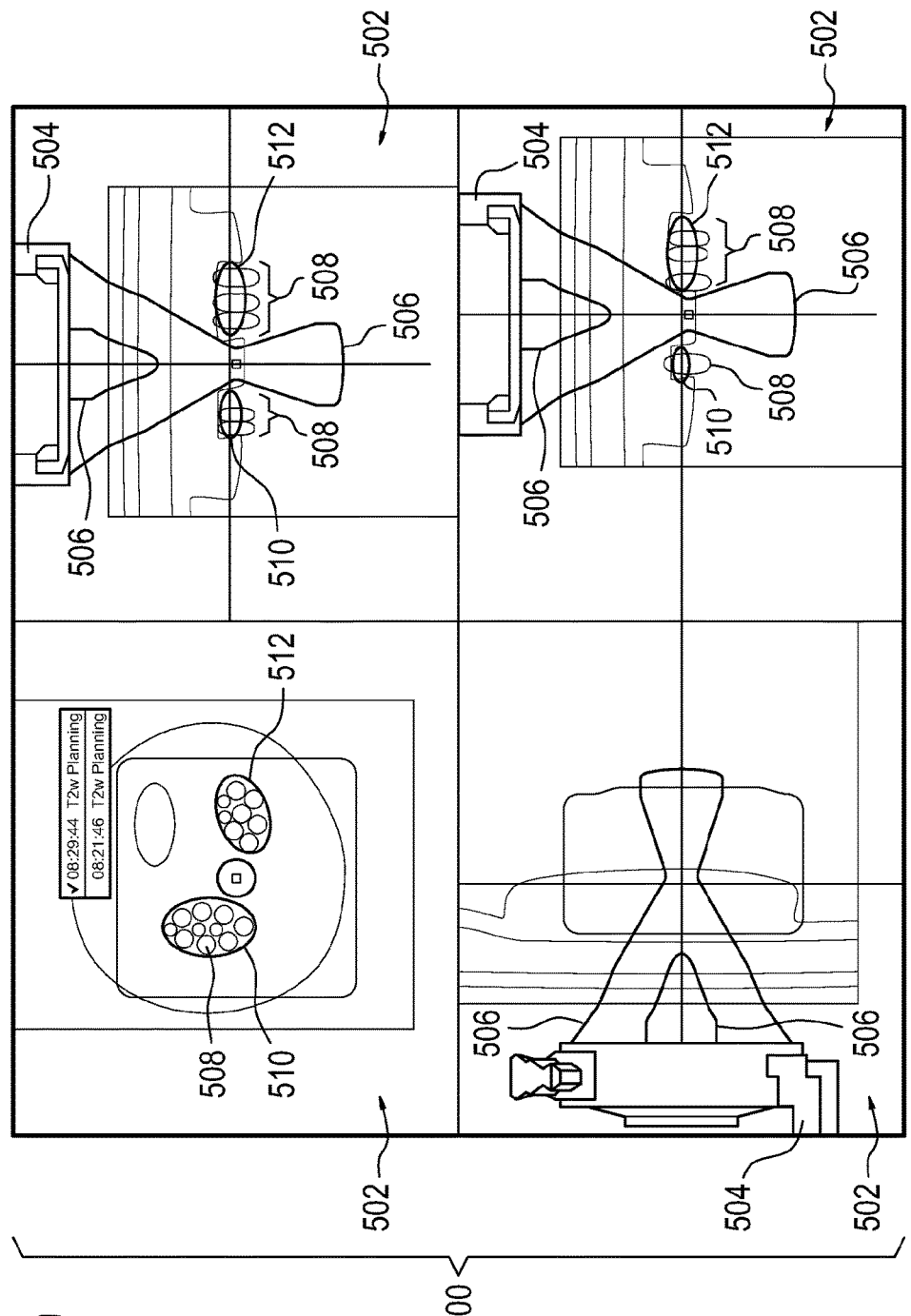
FIG. 9 illustrates a further example of a user interface.

FIG. 9 indicates how the sonication volumes 508 have been repositioned using the new positions of the first graphical object 510 and the second graphical object 512.

In High Intensity Focused Ultrasound (HIFU), patient or organ movement can cause misregistration between already acquired images and the physical patient position. The misregistration can be corrected by the acquisition of new images from the patient and by comparison of the old and new images. Embodiment of the invention may use the already existing graphical HIFU objects, such as the planned target volume, to perform the registration: one of the HIFU planning object is re-positioned on the new image set without a need to first define landmarks or other registration-specific regions of interests.

Registering of image sets acquired at different times with possible patient motion in-between is conventionally arranged with automatic re-registration algorithms or with a landmark-based manual method. These tools typically produce displacement vector field mappings or affine transformations to describe the change in patient position.

Embodiments of the invention may re-use the HIFU planning and treatment graphics to re-register patient position: When new images have been acquired, the positions of HIFU graphical objects on the new images are visually inspected. If discrepancies are found, for example, the fibroid border no longer matches the original planned target volume ellipsoid, the HIFU graphical object is repositioned on one or more 2D slices to register the HIFU plan and possible sonications data to new images. The other HIFU graphical objects are updated and act as verification for the registration.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 medical apparatus
302 magnetic resonance imaging system
304 magnet
306 bore of magnet
308 imaging zone
310 magnetic field gradient coil
312 magnetic field gradient coil power supply
314 radio frequency coil
316 radio frequency transceiver
318 subject
320 subject support
322 computer system
324 hardware interface
326 processor
328 user interface
330 computer storage
332 computer memory
340 pulse sequence
342 first magnetic resonance data
344 first magnetic resonance image
346 multiple graphical objects
348 first group
350 second group
352 image registration
354 second magnetic resonance data
356 second magnetic resonance image
358 repositioning coordinates
359 coordinate transformation
360 control module
362 image reconstruction module
364 coordinate transformation module
400 medical apparatus
402 high intensity focused ultrasound system
404 fluid filled chamber
406 ultrasound transducer
408 mechanism
410 mechanical actuator/power supply
412 path of ultrasound
414 ultrasound window
416 gel pad
417 target zone
418 sonication point
440 treatment plan
450 high intensity focused ultrasound system control module
452 treatment plan modification module
454 image segmentation module
456 user interface control module
500 graphical user interface
502 magnetic resonance image
502' magnetic resonance image
504 high intensity focused ultrasound transducer
506 path of ultrasound
508 sonication volumes
510 first graphical object
512 second graphical object
700 transformation
702 transformation

The invention claimed is:

1. A medical instrument comprising:
a magnetic resonance imaging system and;
an ultrasound system with an adjustable focus,
a processor for controlling the medical instrument; and
a memory containing machine readable instructions for execution by the processor; wherein execution of the instructions causes the processor to
acquire first magnetic resonance data with the magnetic resonance imaging system,
reconstruct a first magnetic resonance image using the first magnetic resonance data,
wherein a treatment plan is formed from the first magnetic resonance image, the treatment plan controlling the ultrasound system
wherein the formation of the treatment plan includes identification of one or more graphical objects in the first magnetic resonance image,
wherein execution of the instructions further causes the processor to
receive a registration of the one or more graphical objects to the first magnetic resonance image, wherein the registration defines spatial positions of the one or more graphical objects with respect to the first magnetic resonance image, and
wherein execution of the instructions further causes the processor to repeatedly:
acquire second magnetic resonance data using the magnetic resonance imaging system;
reconstruct a second magnetic resonance image using the second magnetic resonance data;
receive repositioning coordinates in the second magnetic resonance image for a first group of graphical objects selected from the one or more graphical objects, wherein the repositioning coordinates describe a repositioning of the first group of graphical objects in the second magnetic resonance image with respect to the first magnetic resonance image; and
determine a coordinate transformation of a second group of graphical objects selected from the one or more graphical objects by applying a coordinate transformation model to the repositioning coordinates and
wherein execution of the instructions further causes the processor to repeatedly modify the treatment plan using the repositioning coordinates and the coordinate transformation, and
control the ultrasound system in accordance with the modified treatment plan.

2. The medical instrument of claim 1, wherein the ultrasound system has an adjustable ultrasound intensity, wherein execution of the instructions further causes the processor to perform a sonication before acquisition of the first magnetic resonance data, wherein execution of the instructions causes the processor to check the registration using the first magnetic resonance image.

3. The medical instrument of claim 1, wherein the coordinate transformation model is a deformable shape model.

4. The medical instrument of claim 1, wherein each of the one or more graphical objects has a tag, wherein the coordinate transformation of the second group of graphical objects is determined at least partially using the tag of each of the graphical objects of the second group.

5. The medical instrument of claim 1, wherein the one or more graphical objects are any one of the following: treatment cells, regions of interest, planned target volumes, and combinations thereof.

6. The medical instrument of claim 1, wherein the memory further contains an image segmentation module containing machine readable instructions for execution by the processor for segmenting the second magnetic resonance image to determine the repositioning coordinates, and wherein execution of the instructions further causes the processor to receive the repositioning coordinates from the segmentation module.

7. The medical instrument of claim 1, wherein execution of the instructions further causes the processor to repeatedly display the second magnetic resonance image on a display, and wherein the repositioning coordinates are received from a user interface in response to displaying the second magnetic resonance data.

8. The medical instrument of claim 7, wherein execution of the instructions further causes the processor to display the first magnetic resonance image on the display, and wherein the registration is received from the user interface in response to displaying the first magnetic resonance data.

9. A non-transitory computer-readable medium storing instructions that when executed by a processor cause the processor to execute a method of controlling a medical instrument, wherein the medical instrument comprises a magnetic resonance imaging system for acquiring magnetic resonance data from an imaging zone, and a ultrasound system with an adjustable focus, the method comprising:
    acquiring first magnetic resonance data from the magnetic resonance imaging system;
    constructing a first magnetic resonance image using the first magnetic resonance data;
    forming, from the first magnetic resonance image, a treatment plan for controlling the ultrasound system, the treatment plan including identification of one or more graphical objects in the first magnetic resonance image;
    receiving a registration of the one or more graphical objects to the first magnetic resonance image, wherein the registration defines spatial positions of the one or more graphical objects with respect to the first magnetic resonance image; and
    after the acquiring, constructing, forming and receiving step repeating multiple times the steps of:
        acquiring second magnetic resonance data using the magnetic resonance imaging system;
        constructing a second magnetic resonance image using the second magnetic resonance data;
        receiving repositioning coordinates in the second magnetic resonance image for a first group of graphical objects selected from the one or more graphical objects, wherein the repositioning coordinates describe a repositioning of the first group of graphical objects in the second magnetic resonance image with respect to the first magnetic resonance image;
        determining a coordinate transformation of a second group of graphical objects selected from the one or more graphical objects by applying a coordinate transformation model to the repositioning coordinates;
        modifying the treatment plan using the repositioning coordinates and the coordinate transformation; and
        controlling the ultrasound system in accordance with the modified treatment plan.

10. A method, executed by a processor, of controlling a medical instrument, wherein the medical instrument comprises a magnetic resonance imaging system, and a ultrasound system with an adjustable focus, the method comprising:
    acquiring first magnetic resonance data from the magnetic resonance imaging system;
    constructing a first magnetic resonance image using the first magnetic resonance data;
    forming, from the first magnetic resonance image, a treatment plan for controlling the ultrasound system, the treatment plan including identification of one or more graphical objects in the first magnetic resonance image;
    receiving a registration of the one or more graphical objects to the first magnetic resonance image, wherein the registration defines spatial positions of the one or more graphical objects with respect to the first magnetic resonance image;
    repeatedly acquiring second magnetic resonance data using the magnetic resonance imaging system;
    repeatedly constructing a second magnetic resonance image using the second magnetic resonance data;
    repeatedly receiving repositioning coordinates in the second magnetic resonance image for a first group of graphical objects selected from the one or more graphical objects, wherein the repositioning coordinates describe a repositioning of the first group of graphical objects in the second magnetic resonance image with respect to the first magnetic resonance image;
    repeatedly determining a coordinate transformation of a second group of graphical objects selected from the one or more graphical objects by applying a coordinate transformation model to the repositioning coordinates;
    repeatedly modifying the treatment plan using the repositioning coordinates and the coordinate transformation; and
    repeatedly controlling the ultrasound system in accordance with the modified treatment plan.

11. The method of claim 10, wherein the coordinate transformation model is a deformable shape model.

12. The method of claim 10, wherein each of the one or more graphical objects has a tag and the coordinate transformation of the second group of graphical objects is determined at least partially using the tag of each graphical object of the second group.

13. The method of claim 10, wherein the one or more graphical objects are any one of the following: treatment cells, regions of interest, planned target volumes, and combinations thereof.

14. The method of claim 10, further comprising:
    repeatedly displaying the second magnetic resonance image on a display; and
    receiving the repositioning coordinates from a user interface in response to displaying the second magnetic resonance data.

15. The method of claim 10, further comprising:
    displaying the first magnetic resonance image on a display; and
    receiving the registration from the user interface in response to displaying the first magnetic resonance data.

* * * * *